United States Patent
Farmer et al.

(10) Patent No.: US 10,947,444 B2
(45) Date of Patent: Mar. 16, 2021

(54) MATERIALS AND METHODS FOR REDUCING VISCOSITY OF OIL

(71) Applicant: Locus Oil IP Company, LLC, Solon, OH (US)

(72) Inventors: Sean Farmer, North Miami Beach, FL (US); Ken Alibek, Solon, OH (US); Sharmistha Mazumder, Copley, OH (US); Kent Adams, Twinsburg, OH (US); Tyler Dixon, Kent, OH (US); Yajie Chen, Solon, OH (US); Karthik N. Karathur, Solon, OH (US); Nicholas Callow, Solon, OH (US); Blake Ott, Solon, OH (US); Anthony Nerris, Solon, OH (US)

(73) Assignee: LOCUS OIL IP COMPANY, LLC, Solon, OH (US)

( * ) Notice: Subject to any disclaimer, the term of this patent is extended or adjusted under 35 U.S.C. 154(b) by 0 days.

(21) Appl. No.: 16/477,305

(22) PCT Filed: Feb. 7, 2018

(86) PCT No.: PCT/US2018/017205
§ 371 (c)(1),
(2) Date: Jul. 11, 2019

(87) PCT Pub. No.: WO2018/148265
PCT Pub. Date: Aug. 16, 2018

(65) Prior Publication Data
US 2020/0032128 A1 Jan. 30, 2020

Related U.S. Application Data

(60) Provisional application No. 62/455,903, filed on Feb. 7, 2017, provisional application No. 62/464,046, filed (Continued)

(51) Int. Cl.
C09K 8/582 (2006.01)
C09K 8/584 (2006.01)
(Continued)

(52) U.S. Cl.
CPC .............. *C09K 8/582* (2013.01); *C09K 8/584* (2013.01); *C10G 1/002* (2013.01); *C10G 31/06* (2013.01);
(Continued)

(58) Field of Classification Search
CPC ......... C09K 8/582; C09K 8/584; E21B 43/24; E21B 43/2406; E21B 43/16
See application file for complete search history.

(56) References Cited

U.S. PATENT DOCUMENTS

| 4,450,908 A | 5/1984 | Hitzman |
| 4,522,261 A | 6/1985 | McInerney et al. |

(Continued)

FOREIGN PATENT DOCUMENTS

| CN | 102399547 A | 4/2012 |
| CN | 102766579 A | 11/2012 |

(Continued)

OTHER PUBLICATIONS

Castaneda, L.C., et al., "Current situation of emerging technologies for upgrading of heavy oils." Catalysis Today, 2014, 220-222: 248-273.
(Continued)

*Primary Examiner* — Zakiya W Bates
(74) *Attorney, Agent, or Firm* — Saliwanchik, Lloyd & Eisenschenk

(57) ABSTRACT

The invention provides environmentally-friendly compositions and methods for reducing the viscosity of crude oil using microorganisms and/or biosurfactants produced by microorganisms.

16 Claims, 3 Drawing Sheets

Related U.S. Application Data on Feb. 27, 2017, provisional application No. 62/551,352, filed on Aug. 29, 2017, provisional application No. 62/565,295, filed on Sep. 29, 2017, provisional application No. 62/579,471, filed on Oct. 31, 2017.

(51) Int. Cl.

| | | |
|---|---|---|
| C10G 1/00 | (2006.01) | |
| C10G 31/06 | (2006.01) | |
| C10G 32/00 | (2006.01) | |
| E21B 43/22 | (2006.01) | |
| E21B 43/16 | (2006.01) | |

(52) U.S. Cl.
CPC ............. *C10G 32/00* (2013.01); *E21B 43/16* (2013.01); *C09K 2208/24* (2013.01); *C10G 2300/302* (2013.01)

(56) References Cited

U.S. PATENT DOCUMENTS

| | | |
|---|---|---|
| 4,905,761 A | 3/1990 | Bryant |
| 5,165,477 A | 11/1992 | Shell et al. |
| 6,033,901 A | 3/2000 | Powell, Jr. |
| 7,472,747 B1 | 1/2009 | Brigmon et al. |
| 9,422,470 B2 | 8/2016 | Xu et al. |
| 10,023,787 B2 | 7/2018 | Benoit et al. |
| 2009/0029879 A1 | 1/2009 | Soni et al. |
| 2010/0044031 A1 | 2/2010 | Fallon et al. |
| 2011/0139262 A1 | 6/2011 | Aburto Anell et al. |
| 2012/0122740 A1 | 5/2012 | Roldan Carrillo et al. |
| 2013/0062053 A1 | 3/2013 | Kohr et al. |
| 2013/0324406 A1 | 12/2013 | Chisholm et al. |
| 2015/0037302 A1 | 2/2015 | Bralkowski et al. |
| 2015/0045290 A1 | 2/2015 | Coutte et al. |
| 2016/0251565 A1 | 9/2016 | Yanagisawa et al. |

FOREIGN PATENT DOCUMENTS

| | | |
|---|---|---|
| CN | 104109646 A | 10/2014 |
| CN | 103614131 B | 1/2016 |
| JP | 2010200695 A | 9/2010 |
| WO | 2015167864 A1 | 11/2015 |
| WO | 2016196680 A1 | 12/2016 |
| WO | 2017044953 A1 | 3/2017 |

OTHER PUBLICATIONS

De Almeida, D., et al., "Biosurfactants: Promising Molecules for Petroleum Biotechnology Advances." Frontiers in Microbiology, Oct. 2016, 7(1718): 1-14.

De Brito, D., Biosurfactants from renewable raw materials, Universidade do Minho Departamento de Engenharia Biologica, Nov. 2013, pp. 1-93.

De Oliveira, M., et al., "Review: Sophorolipids A Promising Biosurfactant and it's Applications." International Journal of Advanced Biotechnology and Research, 2015, 6(2): 161-174.

Elshafie, A. E., et al., "Sophorolipids Production by Candida bombicola ATCC 22214 and its Potential Application in Microbial Enhanced Oil Recovery." Frontiers in Microbiology, Nov. 2015, 6(1324): 1-11.

El-Sheshtawy, H.S., et al., "Production of biosurfactants by Bacillus licheniformis and Candida albicans for application in microbial enhanced oil recovery." Egyptian Journal of Petroleum, 2016, 25: 293-298.

Ghojavand, H. et al., "Isolation of thermotolerant, halotolerant, facultative biosurfactant-producing bacteria." Appl. Microbiol. Biotechnol, Oct. 2008, 80(6): Abstract, doi: 10,1007/s00253-008-1570-7.

Gudina, E., et al., "Biosurfactant-producing and oil-degrading Bacillus subtilis strains enhance oil recovery in laboratory sand-pack columns." Journal of Hazardous Materials, 2013, 261: 106-113.

Nitschke, M., et al., "Production and properties of a surfactant obtained from Bacillus subtilis grown on cassava wastewater." Bioresource Technology, 2006, 97: 336-341.

Nur, H.A., et al., "*Saccharomyces cerevisiae* from Baker's Yeast for Lower Oil Viscosity and Beneficial Metabolite to Improve Oil Recovery: An Overview." Applied Mechanics and Materials, 2014, 625: 522-525.

Rocha E Silva, F.C.P., et al., "Yeasts and bacterial biosurfactants as demulsifiers for petroleum derivative in seawater emulsions." AMB Expr., 2007, 7(202): 1-13.

Sen, R., "Biosurfactants: Advances in Experimental Medicine and Biology." Landes Bioscience and Springer Science+Business Media, LLC, 2010, 672: 1-331.

Sharma, A. et al., "A study on biosurfactant production in *Lactobacillus* and *Bacillus* sp." Int. J. Curr. Microbiol. App. Sci., 2014, 3(11): 723-733.

Silva, R., et al., "Applications of Biosurtactants in the Petroleum Industry and the Remediation of Oil Spills." International Journal of Molecular Sciences, 2014, 15: 12523-12542.

Thaniyavarn, J., et al., "Production of Sophorolipid Biosurfactant by Pichia anomala." Bioscience, Biotechnology, and Biochemistry, 2008, 72(8): 2061-2068.

Ines, M., et al., "Glycolipids Biosurfactants; Potential Related Biomedical and Biotechnological Applications." Carbohydrate Research, 2015, 416: 59-69.

| Paraffinic Heavy | Original | Treated | % Increase |
|---|---|---|---|
| API | -3.7 | 7.2 | 295% increase |
| Viscosity | 24,000 cPas | 1,100 cPas | 95% decrease |

| Canadian Syncrude | Original | Treated | % change |
|---|---|---|---|
| API | 16.2 | 32.08 | 100% increase |
| Viscosity | 455 cPas | 43 cPas | 91% decrease |

MATERIALS AND METHODS FOR REDUCING VISCOSITY OF OIL

CROSS-REFERENCE TO RELATED APPLICATIONS

This application is a National Stage Application of International Application No. PCT/US2018/017205, filed Feb. 7, 2018; which claims the benefit of the following U.S. provisional applications: Ser. No. 62/455,903, filed Feb. 7, 2017; Ser. No. 62/464,046, filed Feb. 27, 2017; Ser. No. 62/551,352, filed Aug. 29, 2017; Ser. No. 62/565,295, filed Sep. 29, 2017; and Ser. No. 62/579,471, filed Oct. 31, 2017, each of which is incorporated herein by reference in its entirety.

BACKGROUND OF THE INVENTION

The high demand for fossil fuels necessitates efficient production of oil. A number of challenges in the production of oil derive from the viscosity, surface tension, hydrophobicity and density of crude oil.

Some crude oils have naturally higher viscosities than others. Heavy and extra heavy crude oils are highly viscous with a density close to or even exceeding water. Heavy oils are crudes that have API gravity less than 20° or viscosity higher than 200 cp. Extra heavy oil refers to petroleum with API gravity less than 12° and viscosity higher than 10,000 cp ("Heavy Oil" 2016). Extra-heavy crude oil can be heavier than water and, therefore, can sink to the bottom of a water formation, causing subsurface contamination.

On the other hand, "light" crude oil, or that which has low density and which flows freely at room temperature, has low viscosity and high API gravity due to its higher proportion of light hydrocarbon fractions. Low viscosity crude oils can weather over time into more viscous liquids.

Heavy and extra heavy crude oils are a major potential energy resource. Forty percent of the world's total oil reserves are heavy and extra heavy oil, accounting for 3.6-5.2 trillion bbl of oil. Thus, recovery of these highly viscous hydrocarbons could have major economic significance. However, most heavy and extra heavy oils, asphalts, tars and/or bitumens are highly viscous, and thus, burdensome to transport using conventional methods, such as portable storage tanks and tanker trucks. A significant amount of energy is required to pump oil with higher viscosity through pipelines to refineries and processing facilities.

Heavy oil is also difficult to extract from the ground, due to its viscosity, hydrophobicity and immiscibility with water. Viscosity, in particular, affects the speed at which crude oil can be pumped from a reservoir, with more viscous oils contributing to a decrease in overall productivity for an oil field.

The properties of crude oil also contribute to the difficulty of environmental remediation following, for example, an oil spill onto a body of water. The high interfacial tension causes oil to float on water and adhere to plants, animals and soil. As the aromatic constituents of the oil evaporate, the heavier residues can sink, thereby causing subsurface contamination. Current treatment of spilled oil on water surfaces relies on time-consuming and expensive methods for degrading the oil.

One method of maintaining the flowability of heavy hydrocarbons is to keep them at elevated temperatures. Another well-known method is to mix the heavy oil with a lighter hydrocarbon diluent. This helps to enable, for example, pipeline transportation of the oil. Nonetheless, diluents can be expensive to obtain and transport to oil fields.

Surfactants have also been widely used in the petroleum industry to ameliorate a number of the negative physical properties of crude oil. Surfactant molecules consist of hydrophobic and hydrophilic parts. Their amphiphilic nature allows them to be adsorbed at an oil/water interface, forming micelles that reduce the interfacial tension between the oil and water. The use of chemicals in oil production, however, can result in costs to safety and the environment, as well as for producing and/or obtaining these chemicals.

Efficient production of oil and gas is crucial to meet the high demand for such products. Because of the importance of safe and efficient oil and gas production, the difficulties of producing and transporting heavy crude oil, and the untapped potential of heavy oils to be converted into useful products, there is a continuing need for methods of improving the physical properties of heavy oil, particularly by reducing its viscosity.

BRIEF SUMMARY OF THE INVENTION

The subject invention provides environmentally-friendly, cost-efficient materials and methods for enhancing the recovery and improving the transportation of oil. In specific embodiments, the subject invention provides microbe-based compositions and methods for reducing viscosity of heavy crude oil.

In one embodiment, the subject invention provides microbes, as well as by-products of their growth, such as biosurfactants, solvents, and/or enzymes. The subject invention also provides methods of using these microbes and their by-products.

In certain embodiments, the subject invention provides materials and methods for improving oil production by treating oil-containing sites with a microbe-based composition capable of reducing the viscosity of oil. Advantageously, the subject compositions and methods can be used to improve the viscosity, and/or enhance recovery, of heavy crude oil in "mature" or even "dead" oil reservoirs. Furthermore, in preferred embodiments, the subject invention can be used without increasing the total acid number (TAN) of crude oil.

In preferred embodiments, the microbe-based composition of the present invention comprises cultivated microorganisms and/or their by-products. In one embodiment, the microbe used in the compositions of the subject invention is a biosurfactant-producing bacterium or yeast, or a combination thereof.

In one embodiment, the microorganism is a biosurfactant-producing and/or enzyme-producing "killer yeast," such as, for example, *Pichia guilliermondii* and/or *Pichia anomala* (*Wickerhamomyces anomalus*).

In another embodiment, the microorganism is a yeast selected from one or more *Starmerella* clade yeast strains, which can be effective producers of sophorolipids, and/or one or more strains of *Pseudozyma* yeast, which can be effective producers of mannosylerythritol lipids.

In yet another embodiment the microorganism is one or more *Bacillus subtilis* strains, such as, for example, *B. subtilis* var. *locuses* strains B1 and B2, which are effective producers of surfactin.

In one embodiment, the microbe-based composition can further comprise nutrient sources, including nitrogen, nitrate, phosphorus, magnesium and/or carbon.

In one embodiment, the microbe-based composition comprises a culture that has been aged for 24 hours or longer. Aged culture is culture that has been allowed to rest for a period of time after initial growth and metabolite production has occurred.

In certain embodiments, the compositions of the subject invention have advantages over, for example, biosurfactants alone, including one or more of the following: high concentrations of mannoprotein as a part of a yeast cell wall's outer surface; the presence of beta-glucan in yeast cell walls; the presence of biosurfactants in the culture; and the presence of solvents and other metabolites (e.g., lactic acid, ethanol, ethyl acetate, etc.).

In one embodiment the subject invention provides a method for improving oil recovery by applying to heavy oil, or to an oil recovery site containing heavy oil, the microbe-based composition comprising one or more strains of biosurfactant-producing and/or enzyme-producing microorganisms. The microbe-based composition can reduce the viscosity of the oil; thus, the method improves the ability to recover and/or transport the oil. The method optionally includes adding nutrients and/or other agents to the site in order to, for example, promote microbial growth.

The method may also comprise applying the microbe-based composition with, for example, one or more alkaline compounds, one or more polymer compounds, and/or one or more surfactants.

In one embodiment, the method further comprises the step of subjecting the heavy oil to cavitation either immediately prior to, simultaneously with, and/or sometime after the microbe-based composition has been applied to the heavy oil or oil recovery site. The cavitation can be carried out using machinery known in the art, and can comprise, for example, hydrodynamic or ultrasonic methods.

The cavitation step can be applied to heavy crude oil at any point during the oil recovery and transport chain of operation, for example, after recovery from a well and before being placed in a collection storage tank; during storage; after storage and before being transported in a tanker or pipeline; during transportation; and before the refining process.

The subject methods, including the optional step of cavitation, can also be used for recovering oil from oil sands. The microbe-based composition can be applied to the oil sands, increasing the wettability of the sands and allowing for detachment of the oil from the sands.

In one embodiment, if the oil recovered from oil sands is heavy oil, the method, including the optional step of cavitation, can be applied again to the heavy oil to decrease the viscosity of the oil.

In one embodiment, the subject invention provides methods of producing a biosurfactant by cultivating a microbe strain of the subject invention under conditions appropriate for growth and surfactant production; and purifying the surfactant.

The microorganisms can grow in situ and produce the active compounds onsite. Consequently, a high concentration of, for example, biosurfactant and biosurfactant-producing microorganisms at a treatment site (e.g., an oil well) can be achieved easily and continuously.

In one embodiment, the present invention allows for easier transportation of oil. Once viscosity of heavy oil is reduced, oils can be easily transported by pipeline rather than requiring storage tanks and transportation via trucks.

The microbe-based products of the subject invention can be used in a variety of unique settings because of, for example, the ability to efficiently deliver: 1) fresh fermentation broth with active metabolites; 2) a mixture of cells, spores and/or mycelia and fermentation broth; 3) a composition with vegetative cells, spores and/or mycelia; 4) compositions with a high density of cells, including vegetative cells, spores and/or mycelia; 5) microbe-based products on short-order; and 6) microbe-based products in remote locations.

DETAILED DESCRIPTION

Figure 1A:
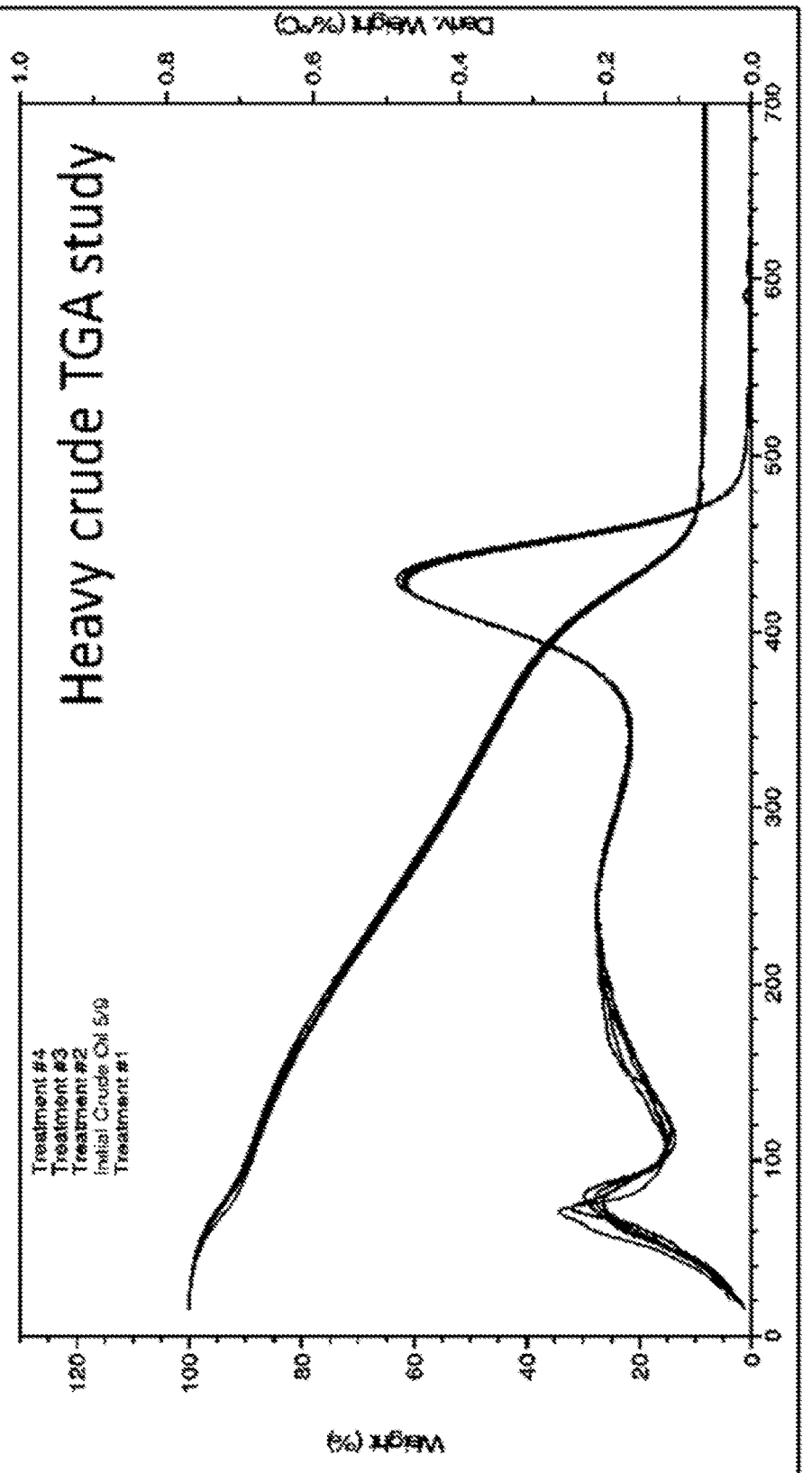
FIGS. 1A-1B show results of a heavy crude TGA study (1A) and BTU increase (1B) after treatment with the subject invention.

The subject invention provides environmentally-friendly, cost-efficient materials and methods for enhancing the recovery and improving the transportation of oil. In specific embodiments, the subject invention provides microbe-based compositions and methods for reducing viscosity of heavy crude oil.

In one embodiment, the subject invention provides microbes, as well as by-products of their growth, such as biosurfactants, solvents, and/or enzymes. The subject invention also provides methods of using these microbes and their by-products.

In certain embodiments, the subject invention provides materials and methods for improving oil production by treating oil containing sites with a microbe-based composition capable of reducing viscosity of crude oil. Advantageously, the claimed compositions and methods can be used to improve the viscosity, and/or enhance recovery, of heavy crude oil in "mature" or even "dead" oil reservoirs.

The subject invention provides advantageous uses for microbes, as well as the by-products of their growth, such as biosurfactants. In certain embodiments, the subject invention provides microbe-based products, as well as their uses in improved oil production. In specific embodiments, the methods and compositions described herein utilize microorganisms to improve the quality of oil by reducing its viscosity.

Advantageously, in one embodiment, the subject invention can be used to convert a heavy asphalt portion of crude oil into lower molecular weight compounds. Furthermore, the subject invention is capable of dissolving asphalt quickly, e.g., overnight, to create a soluble form with greater flammability over the solid form.

In one embodiment, the method further comprises the step of subjecting the heavy oil to cavitation either immediately prior to, simultaneously with, and/or sometime after the microbe-based and/or biosurfactant-based composition has been applied to the heavy oil or oil recovery site. The cavitation can be carried out using machinery known in the art, and can comprise, for example, hydrodynamic or ultrasonic methods.

In one embodiment, the subject invention provides a method for performing oil recovery that comprises applying to an oil recovery site a composition of a biosurfactant-producing yeast, such as a killer yeast, a *Starmerella* yeast, a *Pseudozyma* yeast, and/or a biosurfactant-producing bacteria, such as a strain of *Bacillus subtilis*.

The microbes can be live (or viable), in spore form, or inactive at the time of application. The method can further comprise adding additional materials to enhance microbe growth during application (e.g., adding nutrients to promote microbial growth).

In one embodiment, the microbe-based composition comprises a culture that has been aged for 24 hours or longer. Aged culture is culture that has been allowed to rest for a period of time after initial growth and metabolite production has occurred.

In some embodiments, the *Bacillus subtilis* strains are capable of thriving under low oxygen and/or high salt conditions for the purposes of both enhanced oil recovery and viscosity reduction in a formation. In some embodiments, the *Bacillus subtilis* strain is grown under anaerobic conditions. For example in an oil well treatment system, aerobic fermentation is done first to create a high density of cells and a high concentration of biosurfactants. After injection into the oil well, the strain first grows under aerobic conditions, then micro-aerobic, and then followed by complete anaerobic conditions. Under anaerobic conditions, nitrate salts can be added as the electron acceptor to support the anaerobic respiration.

In one embodiment, this invention provides a yeast fermentation product that can be used to decrease heavy crude oil viscosity. Advantageously, the microbes used in this product do not form biofilms in oil or on oil equipment.

The yeast fermentation product can be obtained via cultivation of a biosurfactant-producing and/or metabolite-producing yeast, such as, for example, *Pichia anomala* (*Wickerhamomyces anomalus*). The fermentation broth after 7 days of cultivation at 25-30° C. can contain the yeast cell suspension and, for example, 4 g/L or more of biosurfactant.

The yeast fermentation product can also be obtained via cultivation of a biosurfactant-producing and/or metabolite-producing yeast, such as, for example, *Starmerella bombicola*. The fermentation broth after 5 days of cultivation at 25° C. can contain the yeast cell suspension and, for example, 100 g/L or more of biosurfactant.

The crude oil can then be incubated with the yeast product for, e.g., 1 day. The viscosity of crude oil after incubation with the yeast fermentation product can be decreased from, for example, $2.3 \times 10^5$ cp to $1.1 \times 10^4$ cp (95% decrease), whereas that incubated with water does not show any clear viscosity drop.

In one embodiment, the yeast fermentation product comprises *Pichia guilliermondii* yeasts.

In one embodiment, the composition according to the subject invention is obtained through cultivation processes ranging from small to large scale. The cultivation process can be, for example, submerged cultivation, solid state fermentation (SSF), and/or a combination thereof.

In one embodiment, the subject invention provides methods of producing a biosurfactant by cultivating a microbe strain of the subject invention under conditions appropriate for growth and surfactant production; and purifying the biosurfactant. The subject invention also provides methods of producing enzymes or other proteins by cultivating a microbe strain of the subject invention under conditions appropriate for growth and protein expression; and purifying the enzyme or other protein.

Advantageously, the present invention can be used without releasing large quantities of inorganic compounds into the environment. Additionally, the compositions and methods utilize components that are biodegradable and toxicologically safe. Thus, the present invention can be used in all possible operations of oil and gas production as a "green" treatment.

Selected Definitions

As used herein, reference to a "microbe-based composition" means a composition that comprises components that were produced as the result of the growth of microorganisms or other cell cultures. Thus, the microbe-based composition may comprise the microbes themselves and/or by-products of microbial growth. The microbes may be in a vegetative state, in spore form, in mycelial form, in any other form of propagule, or a mixture of these. The microbes may be planktonic or in a biofilm form, or a mixture of both. The by-products of growth may be, for example, metabolites, cell membrane components, expressed proteins, and/or other cellular components. The microbes may be intact or lysed. In preferred embodiments, the microbes are present, with broth in which they were grown, in the microbe-based composition. The cells may be present at, for example, a concentration of $1 \times 10^4$, $1 \times 10^5$, $1 \times 10^6$, $1 \times 10^7$, $1 \times 10^8$, $1 \times 10^9$, $1 \times 10^{10}$, or $1 \times 10^{11}$ or more propagules per milliliter of the composition. As used herein, a propagule is any portion of a microorganism from which a new and/or mature organism can develop, including but not limited to, cells, spores, conidia, mycelia, buds and seeds.

The subject invention further provides "microbe-based products," which are products that are to be applied in practice to achieve a desired result. The microbe-based product can be simply the microbe-based composition harvested from the microbe cultivation process. Alternatively, the microbe-based product may comprise further ingredients that have been added. These additional ingredients can include, for example, stabilizers, buffers, appropriate carriers, such as water, salt solutions, or any other appropriate carrier, added nutrients to support further microbial growth, non-nutrient growth enhancers, and/or agents that facilitate tracking of the microbes and/or the composition in the environment to which it is applied. The microbe-based product may also comprise mixtures of microbe-based compositions. The microbe-based product may also comprise one or more components of a microbe-based composition that have been processed in some way such as, but not limited to, filtering, centrifugation, lysing, drying, purification and the like.

As used herein, "harvested" refers to removing some or all of the microbe-based composition from a growth vessel.

As used herein, a "biofilm" is a complex aggregate of microorganisms, such as bacteria, wherein the cells adhere to each other on a surface. The cells in biofilms are physiologically distinct from planktonic cells of the same organism, which are single cells that can float or swim in liquid medium.

As used herein, an "isolated" or "purified" nucleic acid molecule, polynucleotide, polypeptide, protein or organic compound such as a small molecule (e.g., those described below), is substantially free of other compounds, such as cellular material, with which it is associated in nature. As used herein, reference to "isolated" in the context of a microbial strain means that the strain is removed from the environment in which it exists in nature. Thus, the isolated strain may exist as, for example, a biologically pure culture, or as spores (or other forms of the strain) in association with a carrier.

In certain embodiments, purified compounds are at least 60% by weight (dry weight) the compound of interest. Preferably, the preparation is at least 75%, more preferably at least 90%, and most preferably at least 99%, by weight the compound of interest. For example, a purified compound is one that is at least 90%, 91%, 92%, 93%, 94%, 95%, 98%, 99%*, or 100/(w/w) of the desired compound by weight. Purity is measured by any appropriate standard method, for example, by column chromatography, thin layer chromatography, or high-performance liquid chromatography (HPLC) analysis. A purified or isolated polynucleotide (ribonucleic acid (RNA) or deoxyribonucleic acid (DNA)) is free of the genes or sequences that flank it in its naturally-occurring state. A purified or isolated polypeptide is free of the amino acids or sequences that flank it in its naturally-occurring state.

A "metabolite" refers to any substance produced by metabolism or a substance necessary for taking part in a particular metabolic process. A metabolite can be an organic compound that is a starting material (e.g., glucose), an intermediate (e.g., acetyl-CoA) in, or an end product (e.g., n-butanol) of metabolism. Examples of metabolites can include, but are not limited to, enzymes, toxins, acids, solvents, alcohols, proteins, carbohydrates, vitamins, minerals, microelements, amino acids, polymers, and surfactants.

By "modulate" is meant alter (e.g., increase or decrease). Such alterations are detected by standard art known methods such as those described herein.

Ranges provided herein are understood to be shorthand for all of the values within the range. For example, a range of 1 to 20 is understood to include any number, combination of numbers, or sub-range from the group consisting 1, 2, 3, 4, 5, 6, 7, 8, 9, 10, 11, 12, 13, 14, 15, 16, 17, 18, 19, 20, as well as all intervening decimal values between the aforementioned integers such as, for example, 1.1, 1.2, 1.3, 1.4, 1.5, 1.6, 1.7, 1.8, and 1.9. With respect to sub-ranges, "nested sub-ranges" that extend from either end point of the range are specifically contemplated. For example, a nested sub-range of an exemplary range of 1 to 50 may comprise 1 to 10, 1 to 20, 1 to 30, and 1 to 40 in one direction, or 50 to 40, 50 to 30, 50 to 20, and 50 to 10 in the other direction.

By "reduces" is meant a negative alteration of at least 1%, 5%, 10%, 25%, 50°%, 75%, or 100%.

By "reference" is meant a standard or control condition.

By "salt-tolerant" is meant a microbial strain capable of growing in a sodium chloride concentration of fifteen (15) percent or greater. In a specific embodiment, "salt-tolerant" refers to the ability to grow in 150 g/L or more of NaCl.

By "surfactant" is meant a compound that lowers the surface tension (or interfacial tension) between two liquids or between a liquid and a solid. Surfactants act as detergents, wetting agents, emulsifiers, foaming agents, and dispersants.

As used herein, "applying" a composition or product refers to contacting it with a target or site such that the composition or product can have an effect on that target or site. The effect can be due to, for example, microbial growth and/or the action of a biosurfactant or other growth by-product. For example, the microbe-based compositions or products can be injected into oil wells and/or the piping, pumps, tanks, etc. associated with oil wells and oil processing.

As used herein, "heavy oil" or "heavy hydrocarbons" mean viscous hydrocarbon fluids. Heavy hydrocarbons may include highly viscous hydrocarbon fluids such as heavy oil, extra heavy oil, tar, tar sands, fuel oil and/or asphalt. Heavy and extra heavy oils are highly viscous with a density close to or even exceeding water. Heavy hydrocarbons may comprise moderate to high quantities of paraffins, resins and asphaltenes, as well as smaller concentrations of sulfur, oxygen, and nitrogen. Heavy hydrocarbons may also include aromatics or other complex ring hydrocarbons. Additional elements may also be present in heavy hydrocarbons in trace amounts. Heavy hydrocarbons may be classified by API gravity. Heavy hydrocarbons generally have an API gravity below about 20°. Heavy oil, for example, generally has an API gravity of about 10-20°, whereas extra heavy oil generally has an API gravity below about 12°. The viscosity of heavy hydrocarbons is generally greater than about 200 cp at reservoir conditions, and that of extra heavy oil is generally about 10,000 cp or more.

As used herein, "upgrading" or "converting" or "improving the quality of" or "increasing the value of" heavy oil and/or hydrocarbons means changing the structure of the hydrocarbons and/or the contents of the oil in such a way as to increase its overall utility to consumers, and thus, its value to producers. For example, the Btu, i.e., energy or heat content, of the oil can be increased (FIGS. 1A-1B), thus increasing the value of heavy crude before it is sold to refineries. This can also benefit oil refineries who can buy cheaper heavy crude and convert it to a more usable product, such as, for example, road asphalt, using the subject methods and compositions. Upgrading can also involve increasing the API gravity, reducing viscosity, and/or reducing the impurities content of heavy hydrocarbons. Impurity is often a free radical that attaches to large hydrocarbon molecules. Typical impurities found in heavy oil can include, for example, sulfur or hydrogen sulfide, ash, nitrogen, heavy metals, olefins, aromatics, naphthenes, and asphaltenes.

Microbial Strains Grown in Accordance with the Subject Invention

The microorganisms grown according to the systems and methods of the subject invention can be, for example, bacteria, yeast and/or fungi. These microorganisms may be natural, or genetically modified microorganisms. For example, the microorganisms may be transformed with specific genes to exhibit specific characteristics. The microorganisms may also be mutants of a desired strain. Procedures for making mutants are well known in the microbiological art. For example, ultraviolet light and nitrosoguanidine are used extensively toward this end.

In one embodiment, the microorganism is a yeast or fungus. Yeast and fungus species suitable for use according to the current invention, include *Candida*, *Saccharomyces* (*S. cerevisiae, S. boulardii sequela, S. torula*), *Issalchenkia, Kluyveromyces, Pichia, Wickerhamomyces* (e.g., *W. anomalus*), *Starmerella* (e.g., *S. bombicola*), *Mycorrhiza, Mortierella, Phycomyces, Blakeslea, Thraustochytrium, Phythium, Entomophthora, Aureobasidium pullulans, Pseudozyma, Fusarium venenalum, Aspergillus, Trichoderma* (e.g., *T. reesei, T. harzianum, T. hamatum, T. viride*), and/or *Rhizopus* spp.

In one embodiment, the yeast is a killer yeast. As used herein, "killer yeast" means a strain of yeast characterized by its secretion of toxic proteins or glycoproteins, to which the strain itself is immune. The exotoxins secreted by killer yeasts are capable of killing other strains of yeast, fungi, or bacteria. For example, microorganisms that can be controlled by killer yeast include *Fusarium* and other filamentous fungi. Examples of killer yeasts according to the present invention are those that can be used safely in the food and fermentation industries, e.g., beer, wine, and bread making; those that can be used to control other microorganisms that might contaminate such production processes; those that can be used in biocontrol for food preservation; those than can be used for treatment of fungal infections in both humans and plants; and those that can be used in recombinant DNA technology. Such yeasts can include, but are not limited to,

*Wickerhamomyces, Pichia* (e.g., *P. anomala, P. guiellier-mondli, P. kudriavzevii*), *Hansenula, Saccharomyces, Hanseniaspora,* (e.g., *H. uvarum*), *Ustilago maydis, Debaryomyces hansenii, Candida, Cryplococcus, Kluyveromyces, Torulopsis, Ustilago, Williopsis, Zygosaccharomyces* (e.g., *Z. bailii*), and others.

In one embodiment, the microbes are selected from *Pichia* yeast strains. Even more preferably, the yeasts are selected from *Pichia anomala (Wickerhamomyces anomalus), Pichia sydowiorum, Pichia guilliermondii* and *Pichia lyndferdii*.

In specific embodiments, the subject invention provides the use of *Pichia anomala* and/or *Pichia guilliermondii*.

In one embodiment, the microbial strain is *Pseudozyma aphidis* and mutants thereof. *Pseudozyma aphidis* is an effective producer of mannosylerythritol lipids (MELs).

In one embodiment, the microbial strain is chosen from the *Starmerella* clade. A culture of a *Starmerella* microbe useful according to the subject invention, *Starmerella bombicola*, can be obtained from the American Type Culture Collection (ATCC), 10801 University Blvd., Manassas, Va. 20110-2209 USA. The deposit has been assigned accession number ATCC No. 22214 by the depository.

In one embodiment, the subject invention provides the use of yeast strain ATCC 22214 and mutants thereof. ATCC 22214 is an effective producer of SLPs. Procedures for making mutants are well known in the microbiological art. For example, ultraviolet light and nitrosoguanidine are used extensively toward this end.

Other microbial strains including, for example, other fungal strains capable of accumulating significant amounts of, for example, glycolipid-biosurfactants can be used in accordance with the subject invention. Microbial metabolites useful according to the present invention include mannoprotein, beta-glucan and others that have bio-emulsifying and surface/interfacial tension-reducing properties.

In another embodiment, the microorganisms are bacteria, including gram-positive and gram-negative bacteria. The bacteria may be, for example *Bacillus subtilis, Bacillus firmus, Bacillus laterosporus, Bacillus megaterium, Bacillus lcheniformis, Bacillus amyloliquifaciens, Azobacter vinelandii, Pseudomonas chlororaphis* subsp. *aureofaciens* (*Kluyver*), *Agrobacterium radiobacter, Azospirillumbrasiliensis, Azobacter chroococcum, Rhizobium, Sphingomonas paucimobilis, Ralslonia eulropha,* and/or *Rhodospirillum rubrum*. In one embodiment, the microorganism is a strain of *B. subtilis*, such as, for example, *B. subtilis* var. *locuses* B1 or B2. *B. subtilis* is an effective producer of surfactin.

A culture of the *B. subtilis* B1 microbe has been deposited with the American Type Culture Collection (ATCC), 10801 University Blvd., Manassas, Va. 20110-2209 USA. The deposit has been assigned accession number ATCC No. PTA-123459 by the depository and was deposited on Aug. 30, 2016.

The subject cultures have been deposited under conditions that assure that access to the cultures will be available during the pendency of this patent application to one determined by the Commissioner of Patents and Trademarks to be entitled thereto under 37 CFR 1.14 and 35 U.S.C 122. The deposits are available as required by foreign patent laws in countries wherein counterparts of the subject application, or its progeny, are filed. However, it should be understood that the availability of a deposit does not constitute a license to practice the subject invention in derogation of patent rights granted by governmental action.

Further, the subject culture deposits will be stored and made available to the public in accord with the provisions of the Budapest Treaty for the Deposit of Microorganisms, i.e., it will be stored with all the care necessary to keep it viable and uncontaminated for a period of at least five years after the most recent request for the furnishing of a sample of the deposits, and in any case, for a period of at least 30 (thirty) years after the date of deposit or for the enforceable life of any patent which may issue disclosing the cultures. The depositor acknowledges the duty to replace the deposits should the depository be unable to furnish a sample when requested, due to the condition of the deposits. All restrictions on the availability to the public of the subject culture deposits will be irrevocably removed upon the granting of a patent disclosing them.

Growth of Microbes According to the Subject Invention

The subject invention utilizes methods for cultivation of microorganisms and production of microbial metabolites and/or other by-products of microbial growth. The subject invention further utilizes cultivation processes that are suitable for cultivation of microorganisms and production of microbial metabolites on a desired scale. These cultivation processes include, but are not limited to, submerged cultivation/fermentation, solid state fermentation (SSF), and combinations thereof.

The microbial cultivation systems would typically use submerged culture fermentation; however, surface culture and hybrid systems can also be used. As used herein "fermentation" refers to growth of cells under controlled conditions. The growth could be aerobic or anaerobic.

In one embodiment, the subject invention provides materials and methods for the production of biomass (e.g., viable cellular material), extracellular metabolites (e.g. small molecules and excreted proteins), residual nutrients and/or intracellular components (e.g. enzymes and other proteins).

The microbe growth vessel used according to the subject invention can be any fermenter or cultivation reactor for industrial use. In one embodiment, the vessel may have functional controls/sensors or may be connected to functional controls/sensors to measure important factors in the cultivation process, such as pH, oxygen, pressure, temperature, agitator shaft power, humidity, viscosity and/or microbial density and/or metabolite concentration.

In a further embodiment, the vessel may also be able to monitor the growth of microorganisms inside the vessel (e.g., measurement of cell number and growth phases). Alternatively, a daily sample may be taken from the vessel and subjected to enumeration by techniques known in the art, such as dilution plating technique. Dilution plating is a simple technique used to estimate the number of bacteria in a sample. The technique can also provide an index by which different environments or treatments can be compared.

In one embodiment, the method includes supplementing the cultivation with a nitrogen source. The nitrogen source can be, for example, potassium nitrate, ammonium nitrate ammonium sulfate, ammonium phosphate, ammonia, urea, and/or ammonium chloride. These nitrogen sources may be used independently or in a combination of two or more.

The method can provide oxygenation to the growing culture. One embodiment utilizes slow motion of air to remove low-oxygen containing air and introduce oxygenated air. The oxygenated air may be ambient air supplemented daily through mechanisms including impellers for mechanical agitation of the liquid, and air spargers for supplying bubbles of gas to the liquid for dissolution of oxygen into the liquid.

The method can further comprise supplementing the cultivation with a carbon source. The carbon source is typically a carbohydrate, such as glucose, sucrose, lactose, fructose, trehalose, mannose, mannitol, and/or maltose; organic acids such as acetic acid, fumaric acid, citric acid, propionic acid, malic acid, malonic acid, and/or pyruvic acid; alcohols such as ethanol, propanol, butanol, pentanol, hexanol, isobutanol, and/or glycerol; fats and oils such as soybean oil, rice bran oil, olive oil, canola oil, corn oil, sesame oil, and/or linseed oil; etc. These carbon sources may be used independently or in a combination of two or more.

In one embodiment, growth factors and trace nutrients for microorganisms are included in the medium. This is particularly preferred when growing microbes that are incapable of producing all of the vitamins they require. Inorganic nutrients, including trace elements such as iron, zinc, copper, manganese, molybdenum and/or cobalt may also be included in the medium.

In one embodiment, inorganic salts may also be included. Usable inorganic salts can be potassium dihydrogen phosphate, dipotassium hydrogen phosphate, disodium hydrogen phosphate, magnesium sulfate, magnesium chloride, iron sulfate, iron chloride, manganese sulfate, manganese chloride, zinc sulfate, lead chloride, copper sulfate, calcium chloride, calcium carbonate, and/or sodium carbonate. These inorganic salts may be used independently or in a combination of two or more.

In some embodiments, the method for cultivation may further comprise adding additional acids and/or antimicrobials in the liquid medium before, and/or during the cultivation process. Antimicrobial agents or antibiotics are used for protecting the culture against contamination. Additionally, antifoaming agents may also be added to prevent the formation and/or accumulation of foam when gas is produced during cultivation.

The pH of the mixture should be suitable for the microorganism of interest. Buffers, and pH regulators, such as carbonates and phosphates, may be used to stabilize pH near a preferred value. When metal ions are present in high concentrations, use of a chelating agent in the liquid medium may be necessary.

The method and equipment for cultivation of microorganisms and production of the microbial by-products can be performed in a batch, a quasi-continuous process, or a continuous process.

The microbes can be grown in planktonic form or as biofilm. In the case of biofilm, the vessel may have within it a substrate upon which the microbes can be grown in a biofilm state. The system may also have, for example, the capacity to apply stimuli (such as shear stress) that encourages and/or improves the biofilm growth characteristics.

In one embodiment, the method for cultivation of microorganisms is carried out at about 5° to about 100° C., preferably, 15 to 60° C., more preferably, 25 to 50° C. In a further embodiment, the cultivation may be carried out continuously at a constant temperature. In another embodiment, the cultivation may be subject to changing temperatures.

In one embodiment, the equipment used in the method and cultivation process is sterile. The cultivation equipment such as the reactor/vessel may be separated from, but connected to, a sterilizing unit, e.g., an autoclave. The cultivation equipment may also have a sterilizing unit that sterilizes in situ before starting the inoculation. Air can be sterilized by methods know in the art. For example, the ambient air can pass through at least one filter before being introduced into the vessel. In other embodiments, the medium may be pasteurized or, optionally, no heat at all added, where the use of low water activity and low pH may be exploited to control bacterial growth.

In one embodiment, the subject invention further provides a method for producing microbial metabolites such as ethanol, lactic acid, beta-glucan, proteins, peptides, metabolic intermediates, polyunsaturated fatty acid, and lipids. The metabolite content produced by the method can be, for example, at least 20%, 30%, 40%, 50%, 60%, 70%, 80%, or 90%.

The biomass content of the fermentation broth may be, for example, from 5 g/l to 180 g/l or more. In one embodiment, the solids content of the broth is from 10 g/l to 150 g/l.

The microbial growth by-product produced by microorganisms of interest may be retained in the microorganisms or secreted into the liquid medium. In another embodiment, the method for producing microbial growth by-product may further comprise steps of concentrating and purifying the microbial growth by-product of interest. In a further embodiment, the liquid medium may contain compounds that stabilize the activity of microbial growth by-product.

In one embodiment, surfactants are produced by cultivating a microbe strain of the subject invention under conditions appropriate for growth and surfactant production; and, optimally, purifying the surfactant. Enzymes or other proteins can also be produced by cultivating a microbe strain of the subject invention under conditions appropriate for growth and protein expression; and, optimally, purifying the enzyme or other protein.

In one embodiment, all of the microbial cultivation composition is removed upon the completion of the cultivation (e.g., upon, for example, achieving a desired cell density, or density of a specified metabolite in the broth). In this batch procedure, an entirely new batch is initiated upon harvesting of the first batch.

In another embodiment, only a portion of the fermentation product is removed at any one time. In this embodiment, biomass with viable microbes remains in the vessel as an inoculant for a new cultivation batch. The composition that is removed can be a cell-free broth or contain cells. In this manner, a quasi-continuous system is created.

Advantageously, the method does not require complicated equipment or high energy consumption. The microorganisms of interest can be cultivated at small or large scale on site and utilized, even being still-mixed with their media. Similarly, the microbial metabolites can also be produced at large quantities at the site of need.

Advantageously, the microbe-based products can be produced in remote locations. In one embodiment, the microbe-based products can be used for human nutrition and/or disease prevention and/or treatment. The microbe growth facilities may operate off the grid by utilizing, for example, solar, wind and/or hydroelectric power.

Microbe-Based Compositions

The present invention provides compositions for reducing the viscosity of oil. The composition can be used to convert heavy oil to light oil. The composition can further be used to enhance oil recovery, including recovery of oil from oil sands. Furthermore, the composition can be used to improve the transportation of oil by allowing for transport via pipelines rather than storage and transportation tanks.

In certain embodiments, the microbe-based composition of the present invention comprises microorganisms and/or their by-products. In one embodiment, the microbes used in the methods of the subject invention are biosurfactant-producing bacteria or yeasts, or a combination thereof. In one embodiment, the microbe can be one or more *Bacillus subtilis* strains. In another embodiment, the microbe-based composition comprises cultivated *Starmerella bombicola* yeast. In yet another embodiment, the composition comprises cultivated *Pseudozyma aphidis* yeast.

In preferred embodiments, the microorganisms are *Pichia* yeast, such as, for example, *Pichia anomala* (*Wickerhamomyces anomalus*), *Pichia sydowiorum*, *Pichia guilliermondii* and *Pichia lyndferdii*. Most preferably, *Pichia anomala* and/or *Pichia guilliermondii* is used in the microbe-based composition.

In some embodiments, the microbes used according to the subject invention are "surfactant over-producing." For example, the strain may produce at least 0.1-10 g/L, e.g., 0.5-1 g/L surfactant by-products. For example, the microbes produce at least 10%, 25%, 50%, 100%, 2-fold, 5-fold, 7.5 fold, 10-fold, 12-fold, 15-fold or more compared to other oil-recovery microbial strains.

The microbe-based composition can comprise the fermentation broth containing a live culture and/or the microbial metabolites produced by the microorganism and/or any residual nutrients. The product of fermentation may be used directly without extraction or purification. If desired, extraction and purification can be easily achieved using standard extraction and/or purification methods or techniques described in the literature.

Advantageously, in accordance with the subject invention, the microbe-based composition may comprise broth in which the microbes were grown. The product may be, for example, at least, by weight, 1%, 5%, 10%, 25%, 50%, 75%, or 100% broth. The amount of biomass in the product, by weight, may be, for example, anywhere from 0% to 100% inclusive of all percentages therebetween.

The biomass content of the fermentation broth may be, for example from 5 g/l to 180 g/l or more. In one embodiment, the solids content of the broth is from 10 g/l to 150 g/l.

Further components can be added to the microbe-based composition, for example, buffering agents, carriers, other microbe-based compositions produced at the same or different facility, viscosity modifiers, preservatives, nutrients for microbe growth, tracking agents, biocide, other microbes, surfactants, emulsifying agents, lubricants, solubility controlling agents, pH adjusting agents, preservatives, stabilizers and ultra-violet light resistant agents.

In one embodiment, the composition can further comprise buffering agents, including organic and amino acids or their salts to stabilize pH near a preferred value. Suitable buffers include, but are not limited to, citrate, gluconate, tartarate, malate, acetate, lactate, oxalate, aspartate, malonate, glucoheptonate, pyruvate, galactarate, glucarate, tartronate, glutamate, glycine, lysine, glutamine, methionine, cysteine, arginine and mixtures thereof. Phosphoric and phosphorous acids or their salts may also be used. Synthetic buffers are suitable to be used but it is preferable to use natural buffers such as organic and amino acids or their salts.

In a further embodiment, pH adjusting agents include potassium hydroxide, ammonium hydroxide, potassium carbonate or bicarbonate, hydrochloric acid, nitric acid, sulfuric acid and mixtures thereof. The pH of the microbe-based composition should be suitable for the microorganism of interest. In a preferred embodiment, the pH of the microbe-based composition ranges from 7.0-7.5.

In one embodiment, additional components such as an aqueous preparation of a salt as polyprotic acid, such as sodium bicarbonate or carbonate, sodium sulfate, sodium phosphate, or sodium biphosphate, can be included in the microbe-based composition.

Optionally, the product can be stored prior to use. The storage time is preferably short. Thus, the storage time may be less than 60 days, 45 days, 30 days, 20 days, 15 days, 10 days, 7 days, 5 days, 3 days, 2 days, 1 day, or 12 hours. In a preferred embodiment, if live cells are present in the product, the product is stored at a cool temperature such as, for example, less than 20° C., 15° C., 10° C., or 5° C. On the other hand, a biosurfactant composition can typically be stored at ambient temperatures.

In certain embodiments, the compositions of the subject invention have advantages over, for example, biosurfactants alone, including one or more of the following: high concentrations of mannoprotein as a part of a yeast cell wall's outer surface; the presence of beta-glucan in yeast cell walls; the presence of sophorolipids in the culture; and the presence of solvents and other metabolites (e.g., lactic acid, ethanol, etc.).

Known systems in the art can be used to cultivate the microorganisms for use in the present invention, such as submerged culture fermentation, surface culture and hybrid systems. As used herein "fermentation" refers to growth of cells under controlled conditions. The growth could be aerobic or anaerobic.

The product of fermentation may be used directly without extraction or purification. If desired, extraction and purification can be easily achieved using standard extraction methods or techniques known to those skilled in the art.

The method and equipment for cultivation of microorganisms and production of the microbial by-products can be performed in a batch process, a quasi-continuous process, or a continuous process.

The microorganisms in the microbe-based product may be in an active or inactive form. The microbe-based products may be used without further stabilization, preservation, and storage.

Advantageously, direct usage of these microbe-based products preserves a high viability of the microorganisms, reduces the possibility of contamination from foreign agents and undesirable microorganisms, and maintains the activity of the by-products of microbial growth.

The microbes and/or broth resulting from the microbial growth can be removed from the growth vessel in which cultivation occurs and transferred via, for example, piping for immediate use.

In one embodiment, the microbe-based composition comprises a culture that has been aged for 24 hours or longer. Aged culture is culture that has been allowed to rest for a period of time after initial growth and metabolite production has occurred.

In other embodiments, the composition (microbes, broth, or microbes and broth) can be placed in containers of appropriate size, taking into consideration, for example, the intended use, the contemplated method of application, the size of the fermentation tank, and any mode of transportation from microbe growth facility to the location of use. Thus, the containers into which the microbe-based composition is placed may be, for example, from 1 gallon to 1,000 gallons or more. In certain embodiments the containers are 2 gallons, 5 gallons, 25 gallons, or larger.

Upon harvesting the microbe-based composition from the growth vessels, further components can be added as the harvested product is placed into containers and/or piped (or otherwise transported for use). The additives can be, for example, buffers, carriers, other microbe-based compositions produced at the same or different facility, viscosity modifiers, preservatives, nutrients for microbe growth, tracking agents, pesticides, and other ingredients specific for an intended use.

Local Production of Microbe-Based Products

In preferred embodiments of the subject invention, a microbe growth facility produces fresh, high-density microorganisms and/or microbial growth by-products of interest on a desired scale. The microbe growth facility may be located at or near the site of application. The facility produces high-density microbe-based compositions in batch, quasi-continuous, or continuous cultivation.

The distributed microbe growth facilities of the subject invention can be located at the location where the microbe-based product will be used (e.g., a mine) or near the location of use. For example, the microbe growth facility may be less than 300, 250, 200, 150, 100, 75, 50, 25, 15, 10, 5, 3, or 1 mile from the location of use.

Because the microbe-based product is generated locally, without resort to the microorganism stabilization, preservation, storage and transportation processes of conventional microbial production, a much higher density of live microbes in a vegetative or propagule state can be generated, thereby requiring a smaller volume of the microbe-based product for use in the on-site application or which allows much higher density microbial applications where necessary to achieve the desired efficacy. This allows for a scaled-down bioreactor (e.g., smaller fermentation tank, smaller supplies of starter material, nutrients, pH control agents, and de-foaming agents) with no reason to stabilize the cells or separate them from their culture broth, which makes the system efficient and facilitates the transportability of the product.

Local generation of the microbe-based product also facilitates the inclusion of the growth broth in the product. The broth can contain agents produced during the fermentation that are particularly well-suited for local use.

Locally-produced high density, robust cultures of microbes are more effective in the field than those that have undergone vegetative cell stabilization or have sat in the supply chain for some time. The microbe-based products of the subject invention are particularly advantageous compared to traditional products wherein cells have been separated from metabolites and nutrients present in the fermentation growth media. Reduced transportation times allow for the production and delivery of fresh batches of microbes and/or their metabolites at the time and volume as required by local demand.

The microbe growth facilities of the subject invention produce fresh, microbe-based compositions, comprising the microbes themselves, microbial metabolites, and/or other components of the broth in which the microbes are grown. If desired, the compositions can have a high density of vegetative cells or a mixture of vegetative cells, reproductive spores, conidia, and/or mycelia.

Advantageously, the compositions can be tailored for use at a specified location. In one embodiment, the microbe growth facility is located on, or near, a site where the microbe-based products will be used.

Advantageously, these microbe growth facilities provide a solution to the current problem of relying on far-flung industrial-sized producers whose product quality suffers due to upstream processing delays, supply chain bottlenecks, improper storage, and other contingencies that inhibit the timely delivery and application of, for example, a viable, high cell-count product and the associated broth and metabolites in which the cells are originally grown.

Advantageously, in preferred embodiments, the systems of the subject invention harness the power of naturally-occurring local microorganisms and their metabolic by-products to improve oil production. The microbe growth facilities provide manufacturing versatility by the ability to tailor the microbe-based products to improve synergies with destination geographies.

The cultivation time for the individual vessels may be, for example, from 1 to 7 days or longer. The cultivation product can be harvested in any of a number of different ways.

Local production and delivery within, for example, 24 hours of fermentation results in pure, high cell density compositions and substantially lower shipping costs. Given the prospects for rapid advancement in the development of more effective and powerful microbial inoculants, consumers will benefit greatly from this ability to rapidly deliver microbe-based products.

Local microbes can be identified based on, for example, salt tolerance, and ability to grow at high temperatures.

In one embodiment, the composition according to the subject invention is obtained through cultivation processes ranging from small (e.g., lab setting) to large (e.g., industrial setting) scales. These cultivation processes include, but are not limited to, submerged cultivation/fermentation, solid state fermentation (SSF), and combinations thereof.

Advantageously, the microbe-based products can be produced in remote locations. The microbe growth facilities may operate off the grid by utilizing, for example, solar, wind and/or hydroelectric power.

Methods of Enhanced Oil Recovery

In one embodiment the subject invention provides a method for reducing the viscosity of heavy crude oil comprising contacting the microbe-based composition with the oil. The method can be used to convert heavy oil to light oil. The method optionally includes applying nutrients and/or other agents along with the microbe-based composition. The method can be performed in situ by applying the composition and optional nutrients and/or other agents directly in an oil reservoir.

The subject invention can be applied during all stages of the chain of operations, including exploration and production (E&P) operators (e.g., onshore and offshore wellbores, flowlines, and tanks), midstream (e.g., pipelines, tankers, transportation, storage tanks), and in refineries (e.g., heat exchangers, furnaces, distillation towers, cokers, hydrocrackers).

Figures 1B, 2:
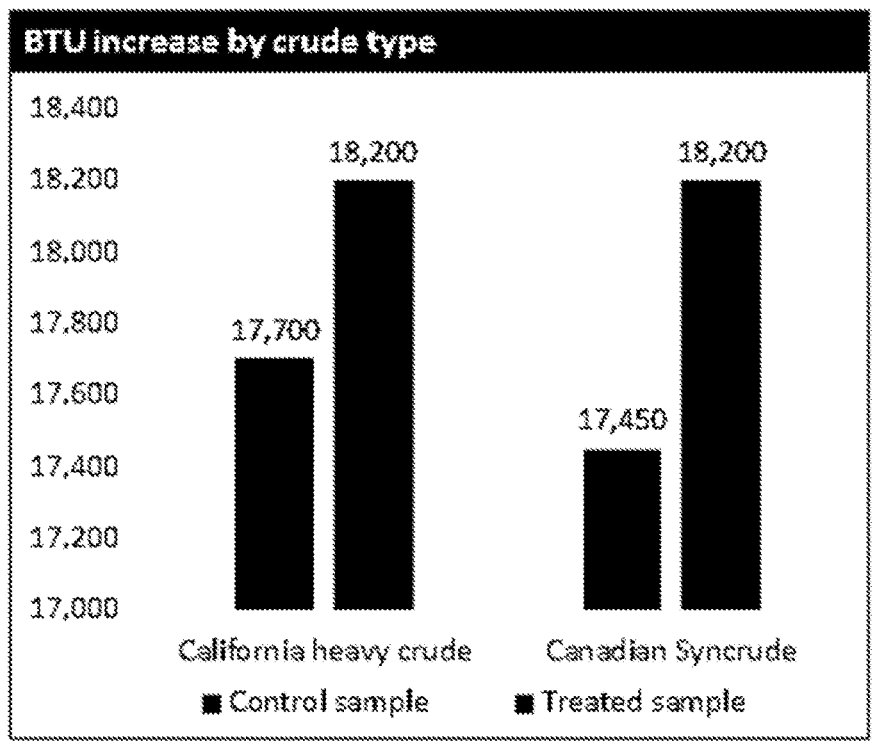
FIG. 2 shows API increase and viscosity reduction after application of the subject treatment.

Advantageously, as shown in FIG. 2, the subject invention can increase the API gravity of crudes, heavy crudes, tar sands and petcokes, as well as reduce or eliminate the need for, and costs associated with, steam injection and other thermal, chemical and mechanical methods of heavy oil extraction. Further reduced or eliminated are the need for diluents (e.g., light or refined crude oil) and water jackets to help move heavy crude through pipelines. Even further, with the reduction of heavy oil viscosity, transportation of oil is less complicated or costly, as the need for tanker trucks and storage tanks is reduced and the use of pipeline transport becomes more feasible.

In one embodiment, the subject invention provides a method of improving oil recovery by applying to an oil recovery site containing heavy oil, the microbe-based composition. The oil recovery site can comprise oil sands. The method optionally includes adding nutrients and/or other agents to the site.

The method may also comprise applying the microbes with one or more alkaline compounds. The alkaline compounds can be selected from, for example, sodium hydroxide, sodium carbonate, sodium hydrogen carbonate, sodium silicate, sodium orthosilicate and combinations thereof.

In some embodiments, the method may also comprise applying the microbe-based composition with one or more polymer compounds. The polymer compounds can be selected from, for example, hydrogels, acrylic acid, acrylamide, polyacrylamide, hydrolyzed polyacrylamide (HPAM), polysaccharide, xanthan gum, guar gum, and cellulose polymers.

In some embodiments, the method may also comprise applying the microbe-based composition with one or more surfactants. The surfactants may be, for example, anionic, cationic, or zwitterionic.

In one embodiment, the method further comprises the step of subjecting the heavy oil to cavitation either immediately prior to, simultaneously with, and/or sometime after the subject microbe-based composition has been applied to the heavy oil. The cavitation can be effected using machinery known in the art, for example, hydrodynamic or ultrasonic cavitation methods.

As used herein, "cavitation" in the context of treating heavy oil means the formation, growth, and collapse or implosion of gas or vapor filled bubbles in liquids. Cavitation requires the presence of small and transient microcavities or microbubbles of vapor or gas, which grow and then implode or collapse. During cavitation of heavy oil, a portion of the liquid comprising the heavy oil is in the form of a gas, which is dispersed as bubbles in the liquid portion. The process effectively destructures the molecular arrangement of heavy hydrocarbons in oil (e.g., asphaltenes, which can form highly associative and cohesive aggregates), thereby reducing its viscosity.

In hydrodynamic cavitation, the liquid comprising the heavy oil is passed through a restriction or cavitation zone, such as, for example, a capillary or nozzle, to increase the velocity of the mixture. The gaseous portion may be present prior to passing the liquid comprising the heavy oil through the cavitation zone and/or such gaseous portion may be produced as a result of the pressure drop that results from passing the liquid comprising the heavy oil through the cavitation zone.

In ultrasonic cavitation, sound waves are propagated into the liquid, resulting in alternating high and low pressure cycles. During the low pressure cycle, high intensity ultrasonic waves create small vacuum bubbles or voids in the liquid. When the bubbles attain a volume at which they can no longer absorb energy, they collapse violently during a high pressure cycle.

The cavitation step according to the subject methods can be applied to heavy crude oil at any point during the oil recovery and transport chain of operation in order to prevent or reduce sedimentation of heavy hydrocarbons in the crude fluids, for example, after recovery from a well and before being placed in a collection tank; during storage; after storage in a collection tank and before being transported in a tanker; during transportation; before the refining process, etc. Cavitation machinery can be attached to a storage tank, tanker truck, pump system, piping, tubing, and/or any other equipment used for transport, transmission and/or storage of crude oil.

Advantageously, the methods can increase the amount of upgraded, usable, and valuable oil products that can be produced from heavy oils, for example, by decreasing the Btu of the heavy oil prior to refining. In other words, because the oil has been treated prior to refining, more useful products such as fuel oils, kerosene, and diesel fuel, and less petcoke, for example, can be produced using less complex refining processes than if the oil were left untreated and highly viscous. Furthermore, in preferred embodiments, the subject invention can be used without increasing the TAN of oil.

In one embodiment, methods are provided for recovering oil from oil sands. Oil sands, tar sands, or bituminous sands, are a type of petroleum deposit comprising either loose sands or partially consolidated sandstone. They can contain a mixture of sand, clay and water, and are typically saturated with dense, highly viscous oil known as bitumen (or tar). To recover oil from oil sands, the microbe-based composition can be applied to the oil sands, increasing the wettability of the sands and allowing for detachment of the oil from the sands. Optionally, heat exchangers or another heat source can be used to warm the process.

According to this method, the sands and other solid particles present in the mixture will settle to the bottom of the mixture, and the oil and other composition liquids can be piped to, for example, a storage tank, where they can further be separated from one another. In one embodiment, the oil sands receive cavitation treatment. In a further embodiment, oil that has been separated from the oil sands is subjected to cavitation treatment.

In one embodiment, the viscosity of the oil recovered from the oil sands can be reduced according to the methods of the subject invention, that is, by applying the subject microbe-based compositions to the oil, optionally followed by subjecting the oil to cavitation.

In one embodiment, the subject invention provides methods of producing a biosurfactant by cultivating a microbe strain of the subject invention under conditions appropriate for growth and surfactant production; and purifying the surfactant.

Microbial biosurfactants are produced by a variety of microorganisms such as bacteria, fungi, and yeasts. Exemplary biosurfactant-producing microorganisms include *Pseudomonas* species (*P. aeruginosa, P. putida, P. florescens, P. fragi, P. syringae*); *Pseudozyma* (*P. aphidis*) *Flavobacierium* spp.; *Pichia* spp. (*P. anomala, P. lynferdii, P. guilliermondii, P. sydowiorum*), *Bacillus* spp. (*B. subtilis, B. amyloliquefaciens, B. pumillus, B. cereus, B. licheniformis*); *Wickerhamomyces* spp. (*W. anomalus*), *Starmerella* spp. (*S. bombicola*), *Candida* spp. (*C. albicans, C. rugosa, C. tropicalis, C. lipolytica, C. torulopsis*); *Rhodococcus* spp.; *Arthrobacter* spp.; *Campylobacter* spp.; *Cornybacterium* spp. and so on. The biosurfactants may be obtained by fermentation processes known in the art.

Safe, effective microbial biosurfactants reduce the surface and interfacial tensions between the molecules of liquids, solids, and gases. As discussed herein, this activity can be highly advantageous in the context of oil recovery.

Biosurfactants are biodegradable and can be easily and cheaply produced using selected organisms on renewable substrates. Most biosurfactant-producing organisms produce biosurfactants in response to the presence of a hydrocarbon source (e.g. oils, sugar, glycerol, etc.) in the growing media. Other media components such as concentration of iron can also affect biosurfactant production significantly.

Biosurfactants according to the subject invention include, for example, low-molecular-weight glycolipids (GLs), lipopeptides (LPs), flavolipids (FLs), phospholipids, and high-molecular-weight polymers such as lipoproteins, lipopolysaccharide-protein complexes, and polysaccharide-protein-fatty acid complexes.

In one embodiment, the microbial biosurfactant is a glycolipid such as a rhamnolipid, sophorolipids (SLP), trehalose lipid or mannosylerythritol lipid (MEL).

In one embodiment, the microbial biosurfactant is surfactin.

In one embodiment, the present invention provides methods of improving transportation of heavy crude oil, comprising contacting the oil with the microbe-based composition and optional nutrients and/or other agents. Once the heavy oil viscosity is reduced, heavy oils can be easily transported by pipeline rather than requiring transportation in storage tanks by trucks.

Further Definitions

The transitional term "comprising," which is synonymous with "including," or "containing," is inclusive or open-ended and does not exclude additional, unrecited elements or method steps. By contrast, the transitional phrase "consisting of" excludes any element, step, or ingredient not specified in the claim. The transitional phrase "consisting essentially of" limits the scope of a claim to the specified materials or steps "and those that do not materially affect the basic and novel characteristic(s)" of the claimed invention.

Unless specifically stated or obvious from context, as used herein, the term "or" is understood to be inclusive. Unless specifically stated or obvious from context, as used herein, the terms "a," "an" and "the" are understood to be singular or plural.

Unless specifically stated or obvious from context, as used herein, the term "about" is understood as within a range of normal tolerance in the art, for example, within 2 standard deviations of the mean. "About" can be understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein are modified by the term about.

The recitation of a listing of chemical groups in any definition of a variable herein includes definitions of that variable as any single group or combination of listed groups. The recitation of an embodiment for a variable or aspect herein includes that embodiment as any single embodiment or in combination with any other embodiments or portions thereof.

Any compositions or methods provided herein can be combined with one or more of any of the other compositions and methods provided herein.

Other features and advantages of the invention will be apparent from the following description of the preferred embodiments thereof, and from the claims. All references cited herein are hereby incorporated by reference.

EXAMPLES

A greater understanding of the present invention and of its many advantages may be had from the following examples, given by way of illustration. The following examples are illustrative of some of the methods, applications, embodiments and variants of the present invention. They are, of course, not to be considered as limiting the invention. Numerous changes and modifications can be made with respect to the invention.

Example 1—Production of *Bacillus subtilis*

Fermentation of *Bacillus subtilis* var. *locuses* can be performed in a 500 L reactor with 350 L of a nutrient medium containing:

| | |
|---|---|
| Glucose | 18 g/L |
| Powder molasses | 2 g/L |
| Sucrose | 1 g/L |
| KH$_2$PO$_4$ | 0.5 g/L |
| Na$_2$HPO$_4$·7H$_2$O | 2.1 g/L |
| KCl | 0.1 g/L |
| MgSO$_4$ | 0.5 g/L |
| CaCl$_2$ | 0.05 g/L |
| Urea | 2.5 g/L |
| NH$_4$Cl | 1.24 g/L |
| Yeast extract | 2 g/L |
| Corn peptone | 0.5 g/L |
| TekNova trace element | 1 mL |

Cultivation can be carried out at 40° C., with pH stabilization from 6.8-7.0, and DO stabilization at 16.8% (concentration of oxygen in the air is taken as 100%) with headspace pressure around 11 psi. Duration of cultivation is 24-32 hours. The final concentration of bacterial culture is no less than 1×10$^9$ CFU/ml. The final surfactin concentration is between 0.5 and 3 g/L.

The amount of culture manufactured by a single fermentation cycle allows for the production of more than 2,000 barrels of final treatment formulation containing 10$^6$ CFU of this strain of *Bacillus*.

Example 2—Fermentation of *Wickerhamomyces* and/or *Pichia* Yeast for Sophorolipid Production in a 450 L Reactor A movable airlift reactor operated by PLC with water filtration, temperature control unit, and air blower for sufficient aeration is used. The process can be carried out as batch cultivation process. The reactor has a working volume of 400 L when growing *Pichia* (e.g., *Pichia anomala*) for SLP production.

In preferred embodiments, the nutrients for SLP production are glucose, urea, yeast extract, canola oil, magnesium sulfate, and potassium phosphate.

Inoculation of this reactor requires up to 5% liquid seed culture of working volume. The duration of the cultivation cycle is 7 days, at a temperature 25° C. and pH 3.5, with sampling performed twice a day.

The final concentration of SLP is roughly 20-25% of the working volume, in this case greater than 90 L of product forms.

Example 3—Fermentation of *Pichia* Yeast for Cell and Single Cell Protein Production in 900 L Reactor A portable reactor divided into two tanks run by a central airlift to help mix the two tanks simultaneously is used. The reactor has a working volume of 600 L when growing *Pichia* yeast (e.g., *Pichia anomala*) for cell production.

In a preferred embodiment, the nutrients for cell production are glucose or baking sugar, urea, yeast extract, magnesium sulfate, and potassium phosphate.

The reactor is inoculated with 2% of seed culture. Fermentation continues for 48-72 hours with no pH stabilization, and a temperature of 26 to 32° C.

The final concentration of cells will be 100 g of wet weight per liter. Wet biomass concentration can reach 90 kilos per cycle with protein concentration up to 45 kilos.

Example 4—Fermentation of *Pichia* Yeast for Cell and Single Cell Protein Production in 2000 L Reactor A portable reactor divided into two square tanks accompanied with 2 loops for mass exchange between them is used. The reactor has a working volume of 2000 L when growing *Pichia* yeast (e.g., *Pichia anomala*) for cell production.

In a preferred embodiment, the nutrients for cell production are glucose or baking sugar, urea, yeast extract, magnesium sulfate, and potassium phosphate.

The reactor is inoculated with 2% of seed culture. Fermentation continues for 48-72 hours with no pH stabilization, and a temperature of 26 to 32° C.

The final concentration of cells will be 100 g of wet weight per liter. Wet biomass concentration can reach up to 200 kilos per cycle with protein concentration up to 100 kilos.

Example 5—Fermentation of *Starmerella bombicola* for Biosurfactant Production in Portable 14 L Reactor This reactor is an autoclavable jacketed glass vessel with air sparger and impeller. It is equipped with dissolved oxygen, pH, temperature, and foam probe; it has an integrated control station with a color touchscreen interface, built-in pumps, gas flow controllers, and pH/DO foam/level controllers.

The working volume of the reactor is 10 liters.

Nutrient medium contains glucose, yeast extract, urea, and vegetable oil. Inoculum can be a 1 to 2-day old culture of *Starmerella bombicola* at about 5-10% of the total culture volume. Cultivation duration and readymade product collection continues for 5-14 days. Final sophorolipid production can reach 1-2 kilogram per cycle.

Example 6—Fermentation of *Starmerella bombicola* for Biosurfactant Production in a Reactor with 2100 L Working Volume A stainless steel, fully enclosed reactor operated by PLC, with water filtration, temperature control unit, and an impeller, is used. The reactor has a working volume of 2100 L when growing *S. bombicola* for SLP production.

In preferred embodiments, the nutrient medium for SLP production comprises glucose, urea, yeast extract, and canola oil.

The reactor is inoculated with 10 liters of liquid culture produced separately in small reactors. The duration of the cultivation cycle for SLP production is 5 days at 25° C. and initial pH 5.5. The pH is then decreased to 3.5 during the process of fermentation.

Each fermentation cycle produces roughly 70-75 gallons of SLP, with a SLP concentration of 300-400 g/L of final product.

Example 7—Fermentation of *Starmerella bombicola* for Biosurfactant Production in 100 L, 110 L and 500 L Reactors The fermenter is an autoclavable jacketed stainless steel vessel with an air sparger and an impeller. It is equipped with dissolved oxygen, pH, temperature, and foam probe; it has an integrated control station with a color touchscreen interface, built-in pumps, gas flow controllers, and pH/DO foam/level controllers. The working volume of 500 L reactor is 350 liters. The working volume of the 110 L reactor is 90 L. The working volume of the 100 L reactor is 60 L.

The nutrient medium contained glucose, yeast extract, urea, and vegetable oil. Inoculum was 1 to 2-day old culture of *Starmerella bombicola* prepared using a 100 L fermenter (5-10% v/v inoculum). Cultivation duration and readymade product collection continued for 5-14 days at 25-30° C. and pH 3.5. The final sophorolipid layer can reach 40% of working volume per cycle. The SLP layer contains 300 to 500 g/L of SLP.

Example 8—Fermentation of *Pseudozyma aphidis* for Mannosylerythritol Lipid (MEL) Production in Portable 14 L Distributable Reactor This is a steam autoclavable jacketed glass vessel with air spurge and Rushton impeller. It is equipped with DO, pH, temperature, and foam probe. It has an integrated control station with a color touchscreen interface, built-in pumps, gas flow controllers, and pH/DO foam/level controllers. The working volume of the reactor is 10 liters.

Nutrient medium composition: Sodium nitrate, Potassium phosphate, Magnesium sulfate, yeast extract, and vegetable oil. Inoculum can be a 1 to 2 day old culture of *Pseudozyma aphidis*, at about 5-10% of the total culture volume. Cultivation duration and sample collection: 9-15 days. Final MEL production: 800-1000 grams.

Example 9—General Protocol for Testing Viscosity Reduction in a Lab Setting

A non-homogenous crude oil sample was collected from a stock bucket by spooning, ladling or pouring into a sealed container for transport. The sample was poured into a beaker and then, if the oil had large visible particulates, it was homogenized using a stick blender for 30 seconds until the sample was visually uniform.

Then, 100 mL of the oil sample was pipetted into a glass bottle with solvent resistant sealing cap. Next, 100 mL of viscosity reducing treatment was added into the bottle (creating a 1:1 ratio of oil to treatment). The threads of the bottle were wrapped with PTFE/Teflon tape, and the cap was securely placed on the bottle to reduce the loss of light volatiles. The bottle was then placed into an orbital shaker. If needed, the bottle can be wrapped in absorbent pads prior to being secured in the shaker.

The bottle containing the mixture was shaken at 70 rpm overnight, or 18±4 h, at a controlled temperature of 30-40° C. After shaking, the sample was allowed to gravity separate for 30 to 60 minutes. If gravity separation is not sufficient or is too slow, the sample can be centrifuged at 8,000 rpm for 30 minutes.

The water layer was removed first so as to ensure collection of a water-free oil layer. Then the oil layer was re-homogenized using the stick blender and collected for viscosity testing. The viscosity was tested at a desired temperature using a rotational viscometer, following standard procedures for the viscometer.

Example 10—Oil Viscosity Reduction Using *Starmerella bombicola* Cultivation Product Extra heavy oil (semi-solid) with a API gravity of −3.7° and a viscosity of 24,000 cPas was used in our study. The heavy oil contains up to 50% solid paraffin.

For heavy oil treatment study, 120 mL heavy crude oil was mixed with 120 mL fermentation culture of *S. bombicola* in 1 L flask. The water control system contained 120 mL heavy crude oil and 120 mL water. The flasks were incubated in the shaker at 30° C. with a shaking speed of 200 rpm for Id. After the treatments, the flasks were removed from the shaker and then centrifuged at 8,000 rpm for 10 mins to let oil water mixture separate into three phases. Light oil phase was on the top layer. Heavy oil phase in the middle and water phase on the bottom of the tube. The top two crude oil phases were sampled and mixed in the oven at 50° C. for 1 day to let the solids dissolve into oil. The oils were then removed from the oven and stored at 21° C. for oil viscosity and API gravity measurements.

Heavy oil viscosity and API gravity were compared between water control and after Id treatment. API gravity increased from −3.7° to 7.2° after treatment for id. Viscosity reduction rate was used to quantify viscosity change. It was found that the heavy oil viscosity decreased from 24,000±3,600 cPas to 1,100-190 cPas, a 95% decrease after Id treatment (FIG. 2), whereas heavy oil viscosity from water system did not show any decrease.

Example 11—Use of Aged *Starmerella bombicola* Culture for Viscosity Reduction A culture of *Starmerella bombicola* was grown in a PLC controlled bioreactor. Temperature and pH were controlled to optimize the production of sophorolipid biosurfactant. The media contained glucose, yeast extract, urea, and vegetable oil. After four days of growth, the sophorolipid in excess of the solubility limit was allowed to settle by gravity. The fermentation broth after biosurfactant settling was then aged over a period of 7 days. Culture broth containing metabolic products was contacted with heavy bitumen oils for 24 hours at a ratio of 1 part treatment to 10 parts oil. Any remaining emulsified water was removed and the viscosity was tested.

Viscosity reduction before water removal was 4% (4,882 cSt to 4,696 cSt). Removal of remaining emulsified water further reduced the viscosity to 57% (4,882 cSt to 2,121 cSt). Water removal alone was only able to reduce the viscosity by 31%, attributing 26% of the reduction to the microbially-derived treatment. Cultures aged 24 hours were not found to reduce viscosity (4,882 cSt to 5,007 cSt).

Example 12—Viscosity Reduction for Colombian Crude Oil Using MEL Composition A sample of residual Columbian crude oil was treated with MEL treatment. If the crude oil was highly non-homogenous, having large visible particulates, the oil was homogenized with a commercial stick blender until smooth and uniform at room temperature. A proportion of MEL treatment was added in different amounts. The sample was mixed by hand at room temperature until the MEL was well incorporated. The viscosity was then tested at 30° C. in a Brookfield style viscometer.

Figure 3:
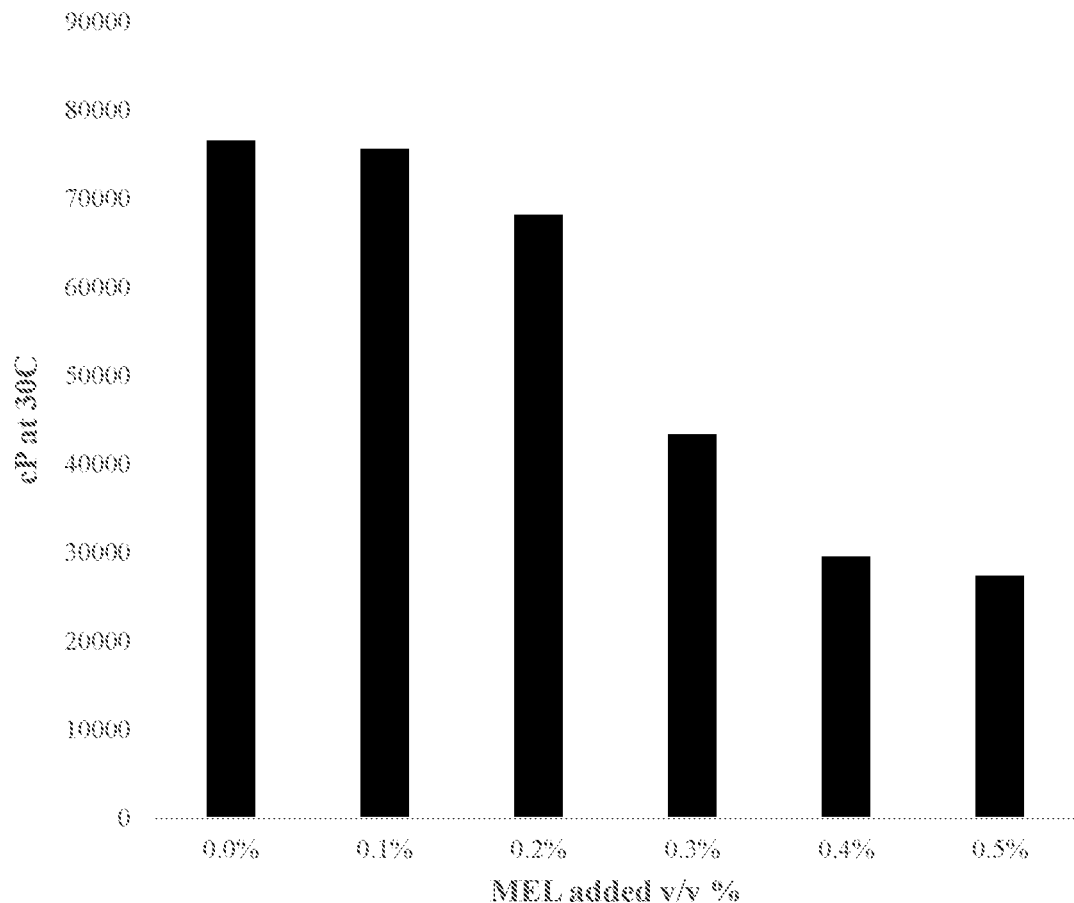
FIG. 3 shows percentage of reduction in viscosity of Columbian Crude oil using MEL treatment. The treatment was successful in reducing the viscosity of the sample by 64%.

The initial sample had a viscosity of 149,460 cp. The addition of MEL reduced the viscosity to 29,530 cp, then to 27,370 cp. A diminishing return on additional MEL from 0.4% to 0.5% may indicate the dissipation of micelles of asphaltenes. This treatment was successful in reducing the viscosity of this sample by 64% (FIG. 3).

Example 13—Viscosity Reduction for Fuel Oil and Bitumen Oil Using MEL Composition Samples of fuel oil and bitumen oil were treated with MEL treatment. If the oil was highly non-homogenous, having large visible particulates, the oil was homogenized with a commercial stick blender until smooth and uniform at room temperature. A proportion of MEL treatment was added in different amounts. Each sample was mixed by hand at room temperature until the MEL was well incorporated. The viscosity was then tested at 30° C. in a Brookfield style viscometer.

For fuel oil, the initial sample had a viscosity of 1,234 cP. Three repeats of 5% MEL treatment were conducted. Each repeat treatment produced a 24% reduction in viscosity (Repeat 1: viscosity reduced to 944 cP; Repeat 2: viscosity reduced to 943 cP; Repeat 3: viscosity reduced to 939 cP).

For bitumen oil, the initial sample had a viscosity of 4,882 cP. Two repeats of 5% MEL treatment were conducted. Each repeat treatment produced a 48% reduction in viscosity (Repeat 1: viscosity reduced to 2,528 cP; Repeat 2: viscosity reduced to 2,533 cP).

Example 14—*Pichia anomala* and Shaker Treatment for Viscosity Reduction

Non-homogeneous crude oil was mixed with a *Pichia anomala* culture grown with 6% canola oil and, optionally, petroleum based inducers comprised of 15% paraffin and 15% bitumen in a canola oil base. Inducers were added at 0.5% (v/v). The culture was mixed 1:1 with the crude oil. The mixtures were placed in an orbital shaker. A temperature of 40° C. was maintained during shaking for 18±4 h. Viscosity was tested at 30° C.

Crude oil shaken at 70 rpm and 40° C. with hydrocarbon induced cultures grown for 3 days yielded a viscosity reduction of 70%±13%. Crude oil shaken at 100 rpm and 40° C. with cultures grown for 3 days had a viscosity reduction of 27%±1%, regardless of the inducers.

Example 15—Test of Various Fractions of *Pichia anomala* Culture for Viscosity Reduction A sample of residual crude oil was treated with fractions of *Pichia anomala* culture treatment. If the crude oil was highly non-homogenous, having large visible particulates, the oil was homogenized with a commercial stick blender until smooth and uniform at room temperature. The crude oil was contacted with a *Pichia anomala* culture grown with 6% canola oil and petroleum-based inducers comprised of 15% paraffin and 15% bitumen in a canola oil base. Inducers were added at 0.5% (v/v).

Different fractions of the culture (listed below in Table 1) were also contacted with the crude oil to obtain their individual contributions to reducing viscosity. The culture or culture equivalent fraction was mixed 1:1 (100 mL:100 mL) with the crude oil.

The samples were shaken overnight at 70 rpm at a temperature of 30° C. Viscosity was tested at 30° C. Viscosity reduction was noted in all cases, with the whole culture producing the most pronounced effect.

TABLE 1

*Pichia anomala* fractions and % reduction in viscosity of crude oil

| Test Component | cP | % reduction |
| --- | --- | --- |
| Homogenized Crude Oil | 65350 | |
| Whole Culture | 4990 | 92% |
| Supernatant and Oil Fraction | 6270 | 90% |
| Cells Only | 23740 | 64% |
| Lysed Cells* | 17400 | 73% |

*100 mL of cells suspended in 50 mL of culture and heated in a 0.1 molar sodium hydroxide solution at 98° C. for 20 minutes.

Example 16—Comparison of Different *Pichia* Microbes for Viscosity Reduction Different *Pichia* yeast strains were tested for their capacity to reduce viscosity of crude oil. Cultures were grown for 3 days at 30° C. in an orbital shaker with 6% canola oil and 0.5% (v/v) of an inducer comprised of 15% paraffin and 15% bitumen in a canola oil base.

All tests were performed at a 1:1 ratio. If necessary, the crude oil was homogenized with a stick blender until smooth. Samples were gently shaken at 30° C. in a capped glass bottle agitated at 70 rpm, overnight. After allowing the oil and water fractions to separate, the oil viscosity was tested at 30° C. As indicated in Table 2, most *Pichia* cultures reduced the viscosity of the homogenized crude. *P. occidentalis* was the only culture that indicated an increase in viscosity.

TABLE 2

% reduction in viscosity of crude oil using various *Pichia* treatments

| Test Condition | cP | % reduction |
| --- | --- | --- |
| Homogenized Crude | 149,460 | |
| Pichia lynferdii | 57900 | 61% |
| Pichia guillermondii | 7462 | 95% |
| Pichia sydowiorum | 49120 | 67% |
| Pichia anomala | 52630 | 65% |
| *Pichia occidentalis | >400,000 | (increase) |

REFERENCES

PetroWiki. Heavy Oil. SPE International; [updated 19 Jan. 2016; accessed 7 Feb. 2017]. http://petrowiki.org/Heavy_oil#cite_note-r1-1. ("Heavy Oil" 2016).

The invention claimed is:

1. A method for reducing the viscosity of oil, wherein the method comprises contacting the oil with a composition that comprises one or more yeasts selected from *Stannerella bombicola, Psendozyma aphidis, Pichia anomala, Pichia sydowiorum, Pichia guilliermondii,* and *Pichia lynferdii;* one or more *biosurfactants;* and fermentation broth in which the one or more yeasts were grown, said fermentation broth comprising metabolites produced by the one or more yeasts.

2. The method of claim, wherein the yeast is selected from *Pichia anomala* and *Pichia guilliermondii.*

3. The method of claim I , wherein the yeast is *Starmerella bombicola.*

4. The method, according to claim 3, wherein the *Starmerella bombicola* is obtained from a culture that has been aged for at least 24 hours.

5. The method of claim 1, wherein the composition comprises a glycolipid biosurfactant selected from sophorolipids (SLPs), rhamnolipids (RLPs), and mannosylerythritol lipids (MELs).

6. The method of claim 5, wherein the composition further comprises surfactin.

7. The method of claim 1, wherein the composition comprises one or more biosurfactants without a microorganism.

8. The method of claim 1, wherein the step of contacting the composition with oil comprises injecting the composition into a wellbore, flowline, or oil tank.

9. The method of claim 1, used to improve oil transmission through an oil field pipe line, tank, casing, tubing, rod, pump, and/or wellbore.

10. The method of claim 1, used to convert a heavy asphalt portion of crude oil into lower molecular weight compounds.

11. The method of claim 1, wherein the composition is produced on-site at a distance not more than 50 miles from the site at which it is used.

12. The method of claim 1, further comprising the step of subjecting the oil to cavitation.

13. A method for recovering oil from oil sands comprising applying a composition that comprises a biosurfactant-producing yeast and/or one or more biosurfactants produced by a yeast to the oil sands; allowing the oil to detach from the sands; and piping out the oil.

14. The method of claim 13, wherein the method further comprises reducing the viscosity of the oil recovered by applying a composition that comprises a biosurfactant-producing yeast and/or one or more biosurfactants produced by a yeast to the oil, and optionally, subjecting the oil to cavitation.

15. The method, according to claim 14, used to improve oil transmission through an oil field pipe line, tank, casing, tubing, rod, pump, and/or wellbore.

16. The method, according to claim 13, wherein the composition comprises a yeast selected from *Starmerella bombicola, Pseudozyma aphidis, Pichia anomala, Pichia sydowiorum, Pichia guilliermondii,* and *Pichia lynferdii;* a biosurfactant selected from sophorolipids (SLPs), rhamnolipids (RLPs), and mannosylerythritol lipids (MELs); and fermentation broth in which the one or more yeasts were grown, said fermentation broth comprising metabolites produced by the one or more yeasts and, optionally, residual nutrients.

* * * * *

UNITED STATES PATENT AND TRADEMARK OFFICE
CERTIFICATE OF CORRECTION

Page 1 of 2

PATENT NO. : 10,947,444 B2
APPLICATION NO. : 16/477305
DATED : March 16, 2021
INVENTOR(S) : Sean Farmer et al.

It is certified that error appears in the above-identified patent and that said Letters Patent is hereby corrected as shown below:

In the Specification

Column 7,
Line 3, "99%*, or 100/(w/w)" should read -- 99%, or 100% (w/w) --.
Line 40, "50°%, 75%," should read -- 50%, 75%, --.

Column 9,
Line 4, "*Cryplococcus,*" should read -- *Cryptococcus,* --.
Lines 40-41, "*Bacillus lcheniformis,*" should read -- *Bacillus licheniformis,* --.

Column 12,
Line 9, "180 g/I" should read -- 180 g/l --.

Column 18,
Lines 34-35, "*Flavobacierium* spp.;" should read -- *Flavobacterium* spp.; --.

Column 22,
Line 66, "rpm for Id." should read -- rpm for 1d. --.

Column 23,
Line 9, "after Id treatment." should read -- after 1d treatment. --.
Lines 14-15, "after Id treatment" should read -- after 1d treatment --.

In the Claims

Column 25,
Lines 41-42, In Claim 1, "*Stannerella bombicola, Psendozyma aphidis,*" should read -- *Starmerella bombicola, Pseudozyma aphidis* --.
Line 44, In Claim 1, "*biosurfactants:*" should read -- biosurfactants; --.
Line 47, In Claim 2, "The method of claim," should read -- The method of claim 1, --.

Signed and Sealed this
Twenty-fourth Day of August, 2021

Drew Hirshfeld
*Performing the Functions and Duties of the
Under Secretary of Commerce for Intellectual Property and
Director of the United States Patent and Trademark Office*

Column 26,
Line 22, In Claim 11, "on-site at a distance" should read -- on-site or at a distance --.